United States Patent [19]

Blanco

[11] 4,391,271

[45] Jul. 5, 1983

[54] RESPIRATOR CIRCUIT

[76] Inventor: Albert Blanco, 3315 SW. 127th Ave., Miami, Fla. 33175

[21] Appl. No.: 251,358

[22] Filed: Apr. 6, 1981

[51] Int. Cl.³ .............................................. A61M 16/00
[52] U.S. Cl. ........................... 128/203.12; 128/205.12; 128/205.27
[58] Field of Search ...................... 128/204.18, 204.21, 128/204.22, 205.12, 205.13, 205.14, 205.15, 205.16, 911

[56] References Cited

U.S. PATENT DOCUMENTS

| | | | |
|---|---|---|---|
| 3,789,837 | 2/1974 | Philips et al. | 128/205.16 |
| 4,020,834 | 5/1977 | Bird | 128/205.14 |
| 4,323,064 | 4/1982 | Hoenig et al. | 128/204.21 |
| 4,327,718 | 5/1982 | Cronenberg | 128/205.12 |
| 4,333,451 | 6/1982 | Paluch | 128/911 |

FOREIGN PATENT DOCUMENTS

| | | | |
|---|---|---|---|
| 2311266 | 9/1974 | Fed. Rep. of Germany | 128/207.15 |
| 520342 | 6/1921 | France | |
| 1456570 | 8/1974 | United Kingdom | |

OTHER PUBLICATIONS

Respiration Technology Corp., sales literature.

Primary Examiner—Henry J. Recla
Attorney, Agent, or Firm—Robert J. Van der Wall

[57] ABSTRACT

The respirator circuit of which the present invention is a part includes a water cascade for humidification of the air, oxygen enriched air or pure oxygen from a conventional respirator. From the cascade a first conduit tube portion connects to a first branch of a Y fitting, a second branch thereof connects a second conduit tube portion to a spirometer, and the main Y fitting leg connects to a conventional endotracheal tube. The improvement that is the focus of this invention is a secondary suction tube or aspirator which is located in close relation to the lowermost main length of the circuit conduits and a plurality of perforations connect between and along the lengths of the main circuit and suction tubes. The suction tube connects to a wall suction inlet as conventionally provided in hospitals, and serves to continuously remove moisture which condenses on the interior wall of the main circuit tubing, either from the cascade, a nebulizer, when used in the circuit with a tracheotomy patient, or excretions from the patient.

24 Claims, 3 Drawing Figures

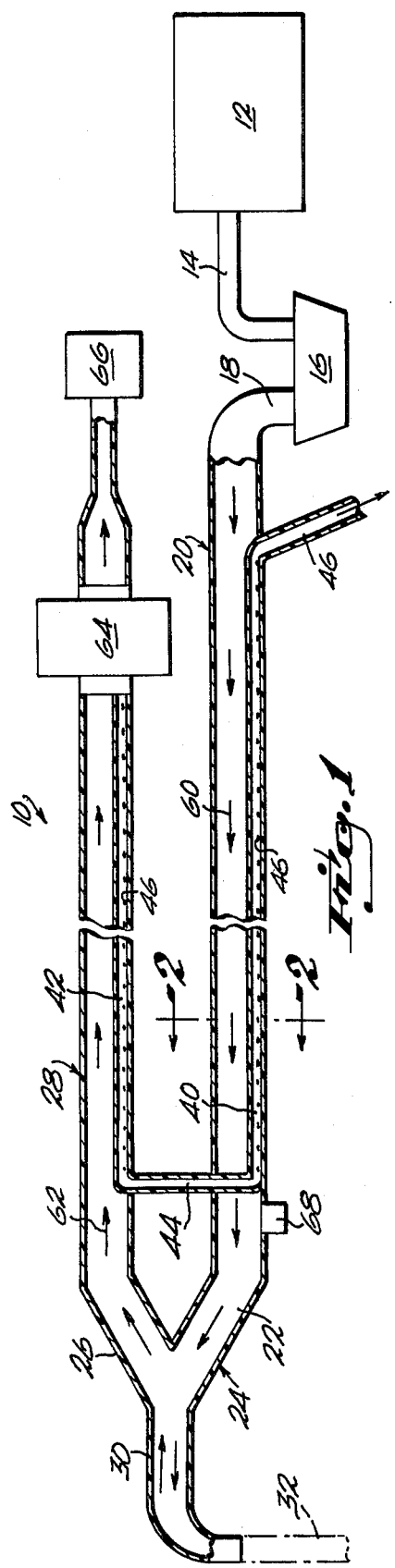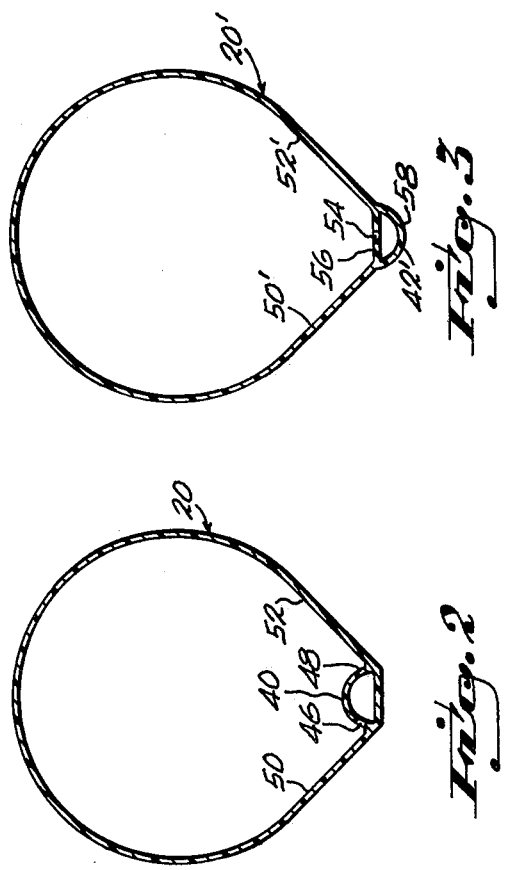

RESPIRATOR CIRCUIT

FIELD OF THE INVENTION

The present invention pertains to an improvement in conventional respirator circuit and more specifically to a circuit of this type which includes means to continuously remove moisture which condenses on the interior walls of the main circuit tubing.

BACKGROUND OF THE INVENTION

Prior art devices, known as respirator circuits, include a water cascade for humidification of the air, oxygen enriched air, or pure oxygen as needed by the patient, supply source of such gases typically known as a respirator. From the cascade, prior art devices include a first conduit tube portion which connects to a first branch of a Y shaped fitting, a second branch thereof which connects a second conduit tube portion to a spirometer and a main Y fitting leg connects to a conventional endotracheal tube. It is well established in the medical arts field that prior art devices of this type must be removed from the patient periodically and drained of condensate if the patient is to avoid asphyxiation by drowning, or insufficient oxygen as a consequence of blockage in the circuit. Those familiar with the actual operation of these devices are aware that drownings of patients have occurred from an over accumulation of condensate in the circuit, although it is probable that such deaths are sometimes attributed to more sophisticated causes inasmuch as simple failure to remove and drain these devices would constitute a virtual admission of actionable negligence.

A search of the prior art by applicant's representatives have disclosed no known art wherein means is incorporated within the respirator circuit to continuously remove condensate to eliminate or substantially reduce the necessity to periodically remove the respirator circuit from the patient to drain that condensate, and which removes condensate along the entire length thereof.

The closest art disclosed by the search are foreign references, namely Bird, United Kingdom Letters Pat. No. 1,456,570, and Drager, French Letters Pat. No. 520,342. The closest art in the United States known to applicant is a device offered for sale by the Respiration Technology Corporation of Chicago, Ill., and termed the SCCR ventilator breathing circuit which includes exhalation and condensate draining valves, upon which device it is alleged that a patent is pending. Even in the latter device, there would not appear to be any means provided for continuous removal of condensate along the entire length of the respirator circuit tubing as is the case with the present invention.

SUMMARY OF THE INVENTION

With the foregoing in mind, it is a principal object of the present invention to provide means to continuously remove the moisture which condenses or collects on the interior walls of the conduit tubing of a respirator circuit, and to do so along substantially all of the respirator circuit conduit length.

A further object of the invention is to provide a secondary drainage tubing within the lowermost portions of, or adjacent to the exterior of the lowermost portions of substantially the entire length of the main circuit tubing of a respirator circuit, with a plurality of perforations connecting therebetween and along the lengths thereof.

A further object of the invention is to connect an extended portion of the drainage tube to a constant suction source, such as is provided in the walls of hospitals.

Another object of the invention is to provide the circuit tubing with appropriate sloping side walls so that condensate therein will flow by gravity forces to the proximity of the suction tube perforations.

A still further object of the present invention is to minimize the risk of cross contamination.

Another object of the invention is to minimize patient-circuit disconnect when using positive-end expiratory pressure (PEEP).

One more object of the invention is to provide temperature stability, which in return provides more laminar flow and less negative resistance which is the direct result of less accumulation of condensate within the tube.

Yet another object of the invention is to provide means to permit a nebulizer to be installed in the circuit, at a point beyond the drainage tube, for use with a mechanical ventilation, but with continuous condensate removal along substantially all of the length of the respirator circuit conduit.

Other objects and advantages of the present invention will be apparent to those skilled in the art.

In accordance with the invention there is provided an improvement in the conduits of a respirator circuit of otherwise conventional construction. A convention respirator circuit includes a water cascade for humidification of the air, oxygen enriched air, or pure oxygen from a conventional respirator. From the cascade a first conduit tube portion connects to a first branch of a Y fitting, a second branch thereof connects a second conduit tube portion to a spirometer, and the main Y fitting leg connects to a conventional endotracheal tube. The improvement that is the focus of this invention is a secondary suction tube or aspirator which is located in close relation to the lowermost main length of the circuit conduits and a plurality of perforations connect between and along substantially the entire lengths of the main circuits and suction tube. The suction tube connects to a wall suction inlet as conventionally provided in hospitals and serves to continuously remove the moisture which condenses on the interior walls of the main circuit tubing, either from the cascade, a nebulizer, when used in the circuit with a tracheotomy patient, or excretions from the patient.

The invention will be better understood upon reference to the detailed description and drawings which:

BRIEF DESCRIPTION OF THE DRAWINGS

FIG. 1 is a generally schematic view of the respirator circuit of the present invention;

FIG. 2 is a substantially enlarged, typical cross sectional view, as seen along line 2—2 of FIG. 1;

FIG. 3 is a view, similar to FIG. 2, of a modified form of the invention.

DETAILED DESCRIPTION

With reference to the drawings, and particularly to FIG. 1, the respirator circuit of the present invention, indicated generally at 10, includes a conventional respirator 12 which connects at 14 to a water cascade 16 which connects at 18 to a first tube portion 20 of the main circuit tubing 10. The water cascade 16 serves to humidify the air, oxygen enriched air, or pure oxygen passing from the respirator into the first tube portion 20 which opens into a first branch 22 of a Y fitting 24. A second branch 26 of the Y fitting 24 connects into a second tube portion 28, and the Y fitting leg 30 connects into a conventional endotracheal tube to a patient, illustrated fragmentarily in phantom at 32.

With reference to FIG. 1, drainage tube portions 40 and 42 extend respectively along bottom portions of tubes 20 and 28 and are interconnected at 44. A plurality of perforations such as 46, 48, FIG. 2, open into the drainage tube portions 40, 42 whereby moisture, which condenses on the interior walls of tube portions 20, 28 is passed into the drainage tubes 40, 42 for disposal through an extension tube portion 46, into a conventional wall suction inlet as provided in hospitals.

With further reference to FIG. 2, the lower side wall portions 50, 52 of tube portions 20, 28 are preferably sharply angled toward the perforations 46, 48 to facilitate a gravity field of condensed moisture therethrough into the drainage tube portions 40, 42.

In the alternative embodiment shown in FIG. 3, the suction tube portions 42' are defined exteriorly of tube portions such as 20'; whereby the condensed moisture is gravity fed down the angled side wall portions 50', 52' and through a plurality of perforations, such as 54, in a web 56, into exterior suction tube portions such as 58.

Pressure forces from the respirator 12 are directed to the patient as indicated by the arrows 60, and the return pressure forces from the patient are directed, as indicated by arrows 62, through a manifold 64 to a spirometer 66 which measures the amount of air entering and leaving the patient's lungs. The manifold 64 stabilizes the air flow therethrough.

A normally closed connection 68 is provided to tube portion 20 to accommodate a nebulizer for use with a tracheotomy patient.

Having described the presently preferred embodiments of the invention, it should be understood that various changes in construction and arrangement will be apparent to those skilled in the art and are fully contemplated there without departing from the true spirit of the invention. Accordingly, there are covered all alternatives, modifications and equivalents as may be included within the spirit and scope of the invention as defined herein by the appended claims.

What is claimed is:

1. A respirator circuit comprising:
    first and second conduit tubes, the cross-section of which has opposed planar lower side portions that are angled oppositely downwardly and inwardly toward drainage means connected thereto, said first and second conduit tubes in open connection respectively to first and second branches of a generally Y-shaped conduit tube portion, including a leg portion for open connection to a conventional endotracheal tube;
    a respirator connected to an end of the first conduit tube through a water cascade to humidify air, oxygen enriched air or pure oxygen passing from the respirator into the first conduit tube;
    the drainage means disposed at a lowermost point of and extending longitudinally along the bottom portions of the first and second conduit tubes, said drainage means being in fluid communication with said first and second conduit tubes through a plurality of perforations opening into the drainage means from the first and second conduit tubes; and
    means to dispose of moisture passing through said perforations into the drainage means from the first and second conduit tubes.

2. The respirator circuit as defined in claim 1 wherein the means to dispose of moisture comprises, an extension from the drainage tube means for a connection to a suitable suction means.

3. The respirator circuit as defined in claim 1 wherein the drainage means are disposed respectively within the first and second conduit tubes.

4. The respirator circuit as defined in claim 1 wherein the plurality of perforations comprises a plurality of spaced apart perforations opening into each side of the drainage means, closely adjacent lowermost interior portions of the conduit tubes.

5. The respirator circuit as defined in claim 1 wherein the drainage means comprises a pair of interconnected drainage tubes disposed exteriorly of the bottom portions of the first and second conduit tubes.

6. The respirator circuit as defined in claim 1 including a spirometer connected to an end of the second conduit tube.

7. The respirator circuit as defined in claim 6 including a manifold connected in the second conduit tube, adjacent the spirometer.

8. The respirator as defined in claim 1 including a normally closed connection in the first conduit tube to accommodate a nebulizer for use with a tracheotomy patient.

9. In an improved respirator circuit having first and second conduit tubes, in open connection respectively to first and second branches of a generally Y-shaped conduit tube portion including a leg portion for open connection to a conventional endotracheal tube, a respirator connected to an end of the first conduit tube, in which the improvement comprises:
    said first and second conduit tubes being of a cross-section having opposed planar lower side portions that are angled oppositely downwardly and inwardly toward drainage means connected thereto;
    the drainage means disposed at a lowermost point of and extending longitudinally along the bottom portions of the first and second conduit tubes, said drainage means being in fluid communication with said first and second conduit tubes through a plurality of perforations opening into the drainage means from the first and second conduit tubes; and
    means to dispose of moisture passing through said perforations into the drainage means from the first and second conduit tubes.

10. The respirator circuit as defined in claim 9 wherein the means to dispose of moisture comprises, an extension from the drainage tube means for a connection to a suitable suction means.

11. The respirator circuit as defined in claim 9 wherein the drainage tube means comprises a pair of interconnected drainage tube portions.

12. The respirator circuit as defined in claim 11 wherein the drainage tube portions are disposed respectively within the first and second tube portions.

13. The respirator circuit as defined in claim 12 wherein the plurality of perforations comprises a plurality of spaced apart perforations opening into each side of the drainage tube portions, closely adjacent lowermost interior portions of the conduit tube portions.

14. The respirator circuit as defined in claim 13 wherein opposed lower side portions of the first and second conduit tube portions are angled oppositely downwardly and inwardly toward the drainage tube means.

15. The respirator circuit as defined in claim 9 wherein the drainage means comprises a pair of interconnected drainage tubes disposed exteriorly of the bottom portions of the first and second conduit tubes.

16. The respirator circuit as defined in claim 9 including a spirometer connected to an end of the second conduit tube.

17. The respirator circuit as defined in claim 16 including a manifold connected in the second conduit tube, adjacent the spirometer.

18. The respirator as defined in claim 9 including a normally closed connection in the first conduit tube to accommodate a nebulizer for use with a tracheotomy patient.

19. In an improved respirator circuit being first and second conduit tubes, in open connection respectively to first and second branches of a generally Y-shaped conduit tube portion including a leg portion for open connection to a conventional endotracheal tube, a respirator connected to an end of the first conduit tube, in which the improvement comprises:

said first and second conduit tubes being of a cross-section having opposed planar lower side portions that are angled oppositely downwardly and inwardly toward drainage tubes connected thereto;

said drainage tubes being interconnected and disposed within the first and second conduit tubes and being in fluid communication therewith through a plurality of perforations the drainage tubes from the first and second conduit tubes; and a means to dispose of moisture having an extension from the drainage tubes for connection to a suitable suction means.

20. The respirator circuit as defined in claim 19 wherein the plurality of perforations comprises a plurality of spaced apart perforations opening into each side of the drainage tubes, closely adjacent lowermost interior portions of the conduit tubes.

21. The respirator circuit as defined in claim 19 wherein the drainage tubes are defined respectively, exteriorly of the bottom portions of the first and second conduit tubes.

22. The respirator circuit as defined in claim 19 including a spirometer connected to an end of the second conduit tube.

23. The respirator circuit as defined in claim 22 including a manifold connected in the second conduit tube, adjacent the spirometer.

24. The respirator as defined in claim 19 including a normally closed connection in the first conduit tube to accommodate a nebulizer for use with a tracheotomy patient.

* * * * *